(12) United States Patent
Haran

(10) Patent No.: US 7,173,690 B2
(45) Date of Patent: Feb. 6, 2007

(54) METHOD AND APPARATUS USING POLARISATION OPTICAL TIME DOMAIN REFLECTOMETRY FOR SECURITY APPLICATIONS

(75) Inventor: Francis M. Haran, North Vancouver (CA)

(73) Assignee: Senstar-Stellar Corporation, Carp (CA)

(*) Notice: Subject to any disclaimer, the term of this patent is extended or adjusted under 35 U.S.C. 154(b) by 294 days.

(21) Appl. No.: 10/611,939

(22) Filed: Jul. 3, 2003

(65) Prior Publication Data
US 2005/0002017 A1  Jan. 6, 2005

(51) Int. Cl.
*G01N 21/00* (2006.01)
(52) U.S. Cl. .................................... 356/73.1
(58) Field of Classification Search ...... None
See application file for complete search history.

(56) References Cited

U.S. PATENT DOCUMENTS

| | | | |
|---|---|---|---|
| 5,144,125 A | 9/1992 | Carter et al. | |
| 5,144,689 A | 9/1992 | Lovely | |
| 5,194,847 A | 3/1993 | Taylor et al. | |
| 5,384,635 A * | 1/1995 | Cohen et al. | 356/73.1 |
| 5,627,927 A * | 5/1997 | Udd | 385/37 |

FOREIGN PATENT DOCUMENTS

| | | |
|---|---|---|
| EP | 0 246 487 | 11/1987 |
| EP | 0 320 255 | 6/1989 |
| EP | 0 638 795 | 2/1995 |
| WO | WO 96/08695 A1 | 3/1996 |
| WO | WO 02/095349 A1 | 11/2002 |

* cited by examiner

*Primary Examiner*—Tu T. Nguyen
(74) *Attorney, Agent, or Firm*—Shapiro Cohen

(57) ABSTRACT

A preferred apparatus and method is presented in which a distributed fiber optic sensor is used in order to detect a disturbance along its length. A pulse of polarized light is launched into an optical fiber; as the pulse propagates along the optical fiber, it continuously loses a small portion of its energy due to Rayleigh backscatter. The Rayleigh backscattered light is analyzed using a polarization sensitive element such as a fiber polarizer. The dynamics of the time dependence of the polarization analyzed backscattered light is used to ascertain if there has been a disturbance along the length of the optical fiber. This technique can be used for applications in areas such as fiber optic telecommunications, perimeter security, fire detection, and pipelines.

23 Claims, 8 Drawing Sheets

METHOD AND APPARATUS USING POLARISATION OPTICAL TIME DOMAIN REFLECTOMETRY FOR SECURITY APPLICATIONS

BACKGROUND OF THE INVENTION

1. Field of the Invention

The present invention relates to a method and apparatus for detecting a disturbance along a length of optical fiber. More specifically, the present invention uses Polarization Optical Time Domain Reflectometry (POTDR) to ascertain if there has been a disturbance along the length of the optical fiber. This technique can be used for security applications in areas such as, but not limited to, fiber optic perimeter security, telecommunications, fire detection, and pipelines.

2. Description of Prior Art

A number of intrusion detection systems are commercially produced. Many of these systems have detection zone lengths from tens of meters up to several kilometers. Oftentimes, these systems will only identify merely whether or not an intrusion has occurred within the detection zone. It would be advantageous with an intrusion detection system to obtain the specific location of the disturbance within the detection zone. Pinpointing such location would enable quicker assessment of the intrusion via either video or human deployment.

Prior art in the field of fiber optic security equipment currently includes polarmetric multimode fiber optic sensors that rely on the differential coupling of light between polarisation states within a multimode optical fiber. When a disturbance occurs along the length of a multimode optical fiber, coupling between both the spatial modes propagating within the fiber and the polarisation eigenstates occur. Prior art fiber optic sensors use a multimode continuous wave laser diode. The system is operated in transmission. FIG. 1 shows a schematic diagram of the relevant optical parts of a fiber optic sensor such as that marketed as IntelliFIBER™ by Senstar-Stellar Corporation of Carp, Ontario, Canada. Polarized light is launched by a pigtailed laser diode 102 into a multimode sensor fiber 103. When the fiber 103 is disturbed, light is coupled between the s- and p-polarisation states. The frequency and strength of the coupling is dependent upon the frequency and strength of the disturbance. The s- and p-polarisation states are defined by the orientation of the plane-of-incidence of the polarisation beam splitter (PBS) cube 105. Transmitted light is emitted from the fiber 103 at a collimator 104 and into the s- and p-polarisation exit ports of the PBS cube 105. Light from the PBS cube 105 is then detected on pin silicon (Si) photodiodes illustrated by p-state detector 101 and s-state detector 106. The difference in the output voltages of the pin Si photodiodes 101, 106 is dependent upon the disturbance such that the difference is processed to identify an intrusion.

Other prior art fiber optic sensors use the redistribution of the energy in the spatial modes on a multimode fiber to detect a disturbance to the fiber. Examples of such include U.S. Pat. No. 5,144,689 issued to Lovely on Sep. 1, 1992 and PCT Publication WO9608695 filed by Tapanes on May 28, 1997. The optical configuration of such prior art sensors is similar to that shown in FIG. 1 except that the PBS is replaced with a modal filter (i.e., aperture). In the case of the prior art of U.S. Pat. No. 5,144,689, the fiber optic sensor includes an inline spacer used between the sensor fiber and a receiver fiber and in the case of PCT Publication WO9608695 a fiber with a smaller core diameter (i.e., single mode fiber) is fusion spliced onto the multimode sensor fiber. Both of these techniques result in a large loss of optical power.

The current prior art sensors as briefly described above are all equally unable to identify the location of disturbances within the detection zone, especially at any specific location along the length of the fiber.

The present invention therefore seeks to provide a fiber optic sensor mechanism that can effectively determine the location of disturbances along a length of optical fiber in a variety of security applications.

SUMMARY OF THE INVENTION

The present invention provides a ranging sensor apparatus for detecting a disturbance at a determinable portion along a length of optical fiber, said apparatus comprising: a transmitter leg for launching a pulsed polarized optical signal; a sensor leg for carrying a portion of said polarized optical signal within said optical fiber; and a receiver leg for accepting a portion of a backscattered optical signal from said sensor leg; wherein said backscattered optical signal provides polarization change and timing information relative to said pulsed polarized optical signal sufficient to determine a location of a disturbance along said optical fiber.

The present invention also provides a method of detecting a disturbance at a determinable portion along a length of optical fiber using backscattered optical signals that provide polarization change and timing information sufficient to determine a location of said disturbance, said method comprising: launching a pulsed polarized optical signal for carrying within an optical fiber; capturing a predetermined number of reflected polarized signal traces from said optical fiber; digitally filtering said predetermined number of reflected polarized signal traces to form a plurality of digitally filtered traces; averaging said digitally filtered traces to form an average trace; obtaining a disturbance trace from said optical fiber; and comparing said disturbance trace to said average trace so as to determine a disturbance at a portion of said optical fiber.

The present invention also provides a hybrid audio/location sensor apparatus for detecting a disturbance at a determinable portion along a length of cabling including a locating optical fiber and a non-locating sensor cable, said apparatus comprising: a transmitter leg for launching a pulsed polarized optical signal; a sensor leg for carrying a portion of said polarized optical signal into said optical fiber; a receiver leg for accepting a portion of a backscattered optical signal from said sensor leg; and an audio processor for providing an audio output indicative of a disturbance along said non-locating sensor cable; wherein said backscattered optical signal provides polarization change and timing information relative to said pulsed polarized optical signal sufficient to determine a location of a disturbance along said optical fiber.

The present invention also provides a sensor leg comprising a hybrid cable including: an optical fiber for carrying a backscattered optical signal providing polarization change and timing information relative to a pulsed polarized optical signal sufficient to determine a location of a disturbance along said optical fiber, and a non-locating sensor cable for generating or modifying a signal capable of being processed into an audio output indicative of a disturbance along said non-locating sensor cable; wherein said optical fiber and said non-locating sensor cable may be physically integrated within a single jacketing.

DETAILED DESCRIPTION OF THE INVENTION

Figure 1:
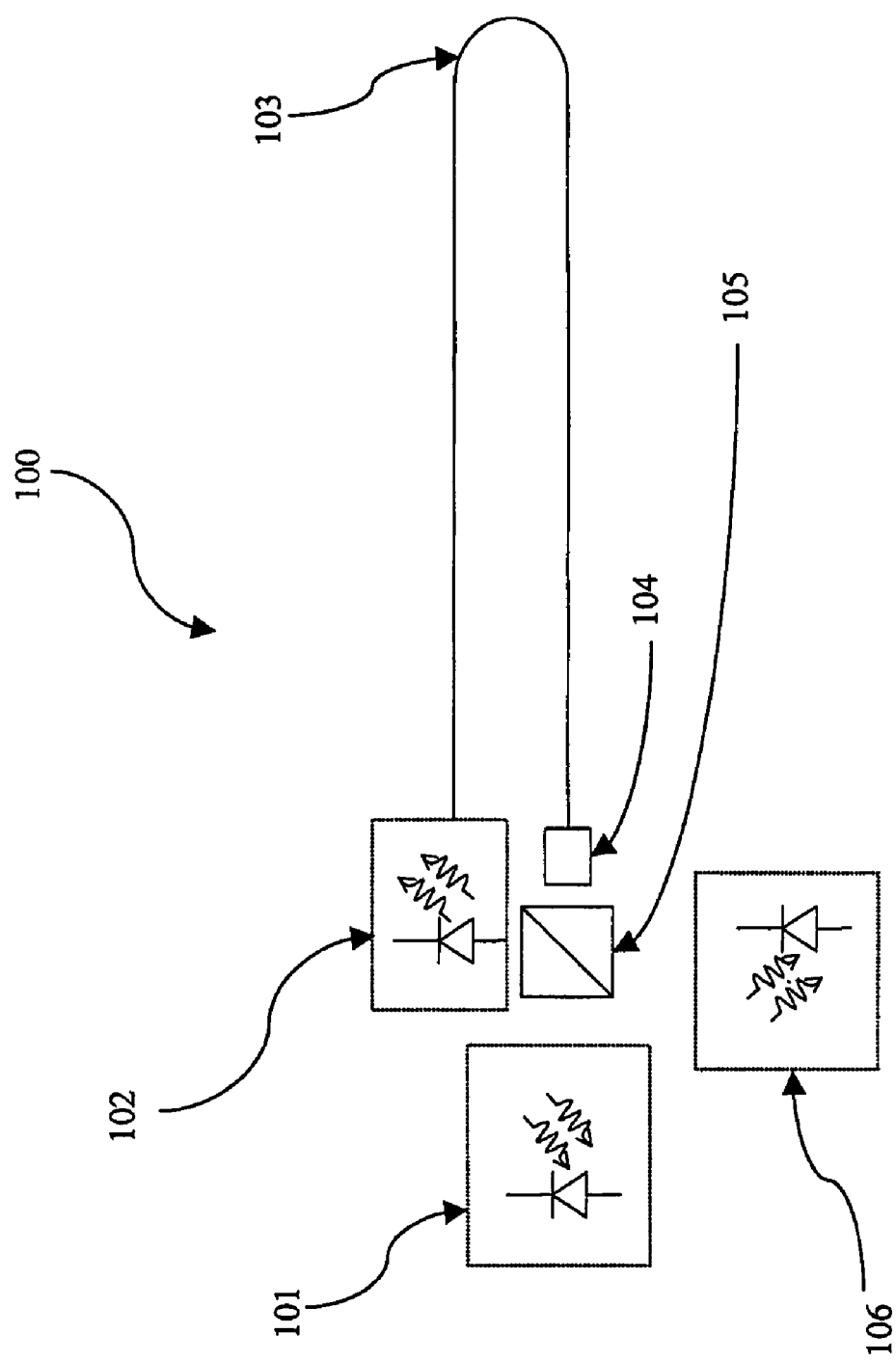
FIG. 1 is a schematic of a prior art multimode polarmetric intrusion sensor.

The invention will be described for the purposes of illustration only in connection with certain embodiments; however, it is to be understood that other objects and advantages of the present invention will be made apparent by the following description of the drawings according to the present invention. While a preferred embodiment is disclosed, this is not intended to be limiting. Rather, the general principles set forth herein are considered to be merely illustrative of the scope of the present invention and it is to be further understood that numerous changes may be made without straying from the scope of the present invention.

The present invention improves upon the prior art that cannot identify the location of disturbances within the detection zone. The present invention is an outcome of an investigation into the use of fiber optic time domain reflectometer techniques to locate targets along the length of an optical fiber for security applications. In fiber optic time domain reflectometer systems, a temporal pulse (typically 10 nanoseconds (ns) to 10 milliseconds (ms)) of light is launched into an optical fiber. As this pulse propagates in the optical fiber, some of its energy is backscattered from the microscopic inhomogeneities that are "frozen" into all optical fibers at the time of manufacture. The optical characteristics of the backscattered light are dependent upon the fibers' physical and optical properties.

Information on the physical and optical properties of the fiber can be obtained as a function of fiber length by analyzing the optical properties of the backscattered light in the temporal domain. Further, if the local properties of an optical fiber (via intruder induced perturbations) are dynamically changed, then analysis of the backscattered light can be used to locate a disturbance along the length of the fiber. The intensity, optical phase, and relative polarisation are the three main properties of the backscattered light that can be analyzed. For purposes herein, the term relative polarization means relative to the temporal polarisation state at some prior time—i.e., between $t_1$ and $t_2$, or the before and after disturbance traces. Optical instruments that analyze the phase, polarisation, and intensity of the backscattered light utilize Coherent Optical Time Domain Reflectometry (COTDR), a Polarization Optical Time Domain Reflectometry (POTDR), and an Optical Time Domain Reflectometry (OTDR), respectively.

Phase and intensity are respectively the most and least sensitive optical properties of the backscattered light. Of the three optical time domain reflectometry techniques, a POTDR based system was determined most suitable for the intruder detection application due to their sufficient sensitivity for security applications and their use of a relatively inexpensive and reliable laser source. An OTDR based system does not have sufficient sensitivity to allow a simple mechanical cable design and fence attachment system. A COTDR based system would easily have sufficient sensitivity for such security applications, but such systems are very expensive and include unreliable laser sources. While some newer fiber laser sources have recently entered the marketplace that may eventually provide cheaper and certainly more reliable laser sources in the future, such newer devices are still significantly more expensive and more unreliable than a POTDR based source.

Figure 2:
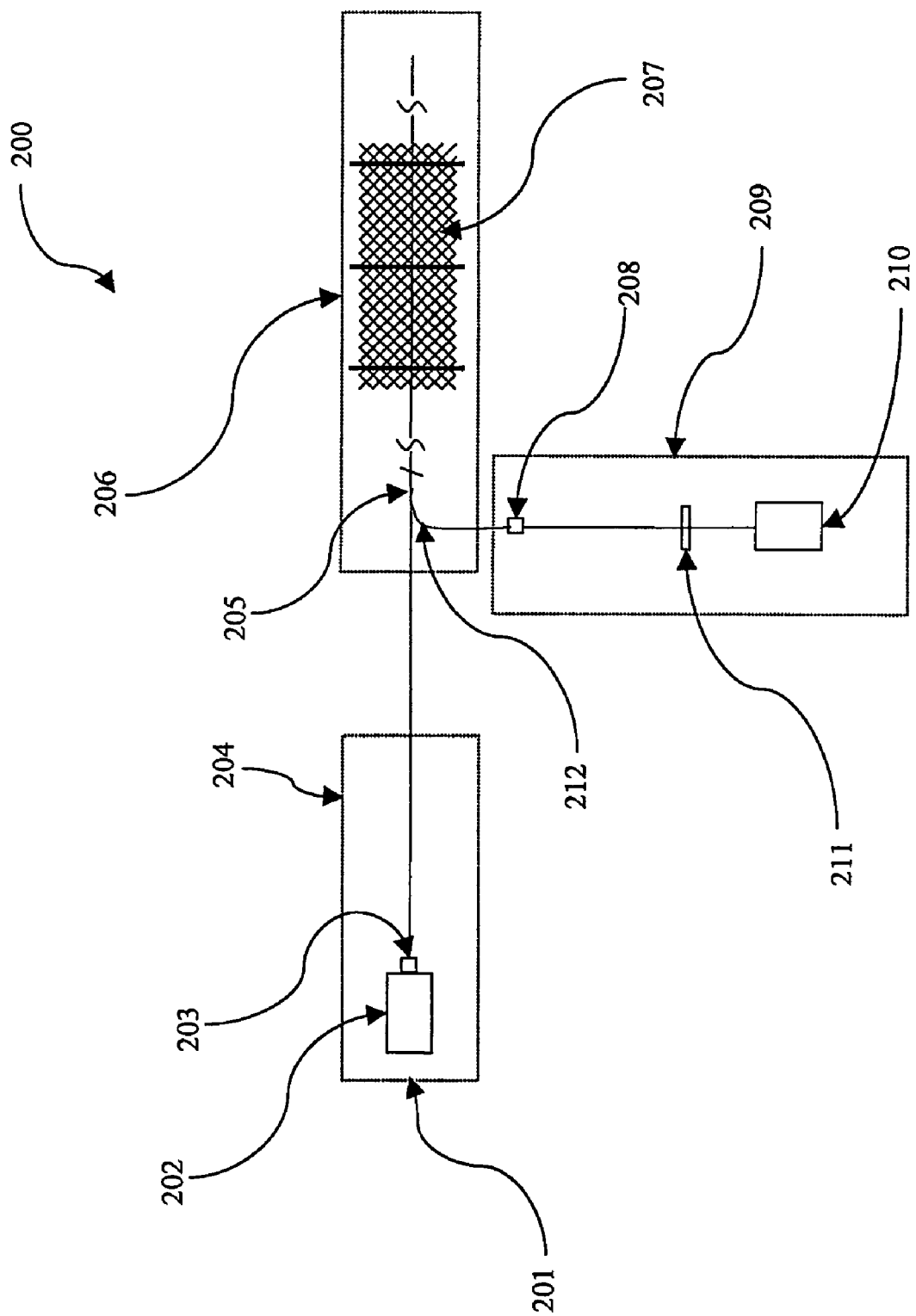
FIG. 2 is a POTDR fiber optic ranging system for intruder detection in accordance with a first preferred embodiment of the present invention.

A number of configurations for a POTDR intrusion location system are possible, however one of the more straightforward configurations is initially discussed with reference to the schematic diagram of a POTDR based intrusion detection system 200 as shown in FIG. 2.

With reference to FIG. 2, light from a pulsed polarized light (i.e., laser) source 202 is launched from a transmitter leg 204 via connector 203 into one arm of a 50:50 fiber optic directional coupler 212. It should be readily understood that a fiber optic circulator could also be used (see FIG. 4 described further hereinbelow). The pulsed laser source 202 is typically a solid-state semiconductor laser diode operating at a center wavelength of 1550 nanometers (nm) with a Full Width Half Maximum (FWHM) spectral linewidth from around 1 nm to as much as 10 nm. Ideally, the linewidth of the source should be around 1 nm in order to avoid too much depolarisation of the light as it propagates along the optical fiber. In order to avoid excessive depolarisation, a fiber with a small polarisation mode dispersion (PMD) value should be chosen (e.g., a standard single mode fiber such as "Corning SMF28" produced by Corning Corporation of Corning, N.Y., US). Sources with linewidths substantially smaller than 1 nm should also be avoided as coherent noise problems may occur. The use of sources with center wavelengths around 1550 nm will also allow an extended range of the present invention because this wavelength is compatible with optical amplifiers such as those based on Erbium doped optical fiber. The 1550 nm wavelength is also compatible with PMD compensators, which will again extend the range of the present invention. The attenuation of silica based communications fiber is also minimal at 1550 nm. Other source wavelengths that may be used include those around 1300 nm, 850 nm, and 905 nm.

With continued reference to FIG. 2, half of the launched light then propagates along the sensor fiber typically arranged along a perimeter fence 207. While a fence 207 is illustrated, it should be readily understood that any suitable carrier mechanism may be used to support the sensing fiber along the sensor leg 206. The back-scattered light propagates from the sensor fiber to the directional coupler 212 where a portion of the backscattered light is tapped off into the receiver leg of the POTDR via connector 208. An in-line fiber optic polarizer 211 is located in the receiver leg 209 before a receiver 210 including a photodiode with an amplifier that detects the backscattered light. The receiver 210 may include an avalanche photodiode, a pin photodiode, a photomultiplier tube, or any suitable receiving element. The output of the receiver 210 as a function of time is dependent upon the local state of polarisation (SOP) of the light along the length of sensor fiber. If the sensor fiber is disturbed at any particular point along the length of fiber within the sensor leg 206, then the temporal output from the photodiode will change because the SOP at that point changed. Typically the magnitude of the backscattered power is very low and a certain number of POTDR traces are averaged. Also, filtering can be employed to reduce the noise or unwanted signal from the POTDR traces.

It should be clear that the primary element of the sensor leg in any of the various embodiments disclosed herein is a cable. Such cable could be any combination of separate or integrated sensing cables, ranging or non-ranging cables, or audio cables, and may be formed of several different materials including, but not limited to, triboelectric, magnetic, piezoelectric, electret, and the like.

Still further, it should be understood that while the backscattered optical signal provides polarization change and timing information relative to the pulsed polarized optical signal sufficient to determine a location of a disturbance along the optical fiber, the actual disturbance is detected by sensing changes between sets of sampled traces or time waveforms. In this regard, the polarization change and timing information should be understood to include changes between sets of sampled traces or time waveforms, not just timing information from the start of a pulse on one waveform.

Figure 3:
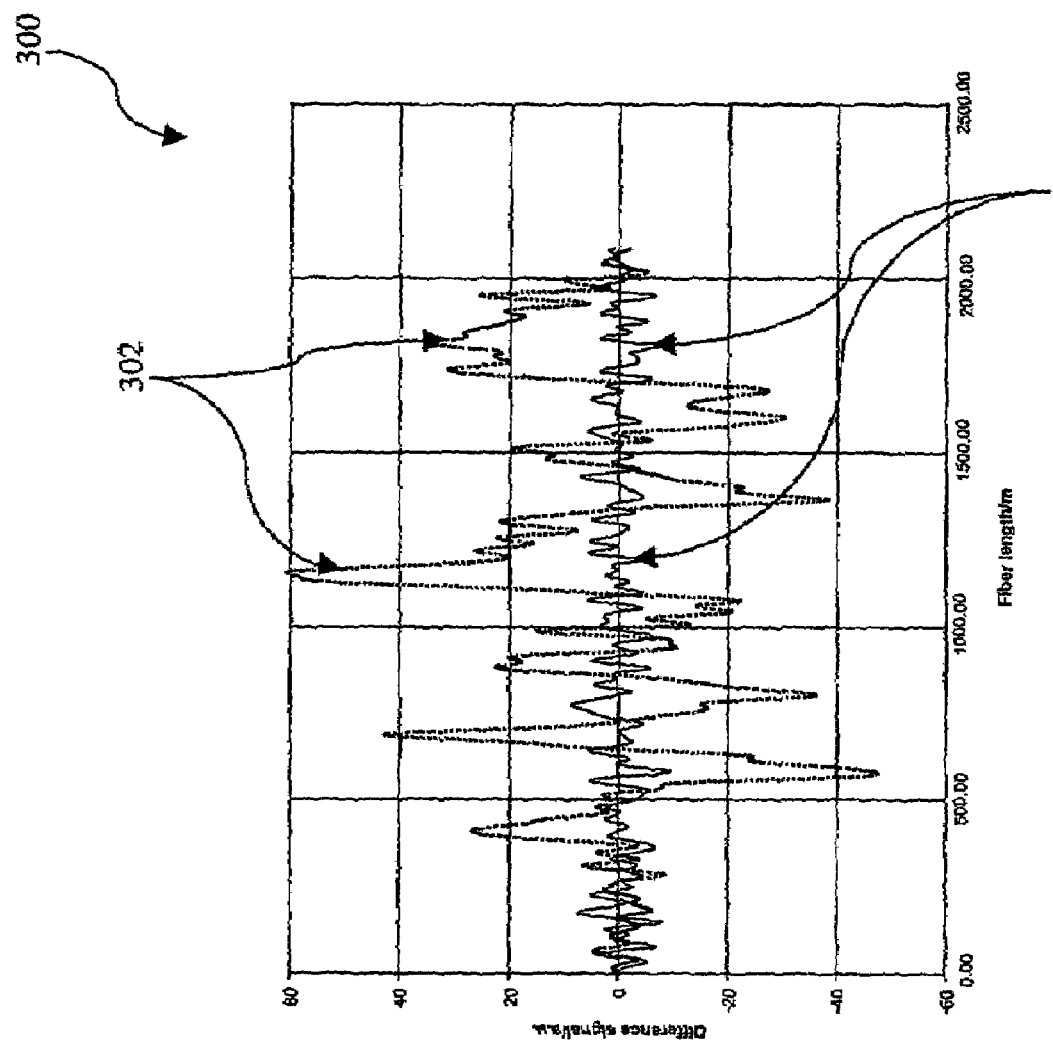
FIG. 3 is a graph showing POTDR difference signals with and without disturbances for the system as shown in FIG. 2.

It should be understood that the output (i.e., POTDR signal) of the receiver 210 is processed via any suitable computing means such as, but not limited to, a personal computer, laptop, customized microprocessor-based unit, or the like. One method of processing the POTDR signals for intruder detection is to capture a number of POTDR traces, then digitally filter, average them, and later repeat the process. From the difference between these two resultant processed POTDR traces, it is seen whether there has been a disturbance along the length of fiber. The graph 300 in FIG. 3 shows plots of the POTDR difference signals along a sensing fiber length with a disturbance 302 and without a disturbance 301. It can be seen from FIG. 3 that if a threshold of, for example, 10 a.u. (arbitrary units) is applied to the difference signal, then the disturbance at approximately 370 m distance from the input end of the fiber will be detected. Note however, that if there were multiple simultaneous disturbances along the fiber, then only the first disturbance would be detected. The number of averages taken for each POTDR trace will typically be between 2 and 1000, however a single trace may give acceptable results for short range or if there is a sufficient signal-to-noise ratio. The POTDR traces are typically filtered using a software digital filter or a hardware-implemented filter. The time period between the two filtered and averaged POTDR traces is a variable and can typically range from milliseconds to 0.5 seconds. This typical time period is based on rapid response requirements for video assessment such as when the intruder is still on the fence. If such rapid response is not required, then the time period could usefully be longer in terms of seconds. Any reference trace (without disturbance) only has to be taken on the scale of the ambient thermal and mechanical time constant. One may therefore only have to take the reference trace every five minutes, for example, or after a positive disturbance reading.

The present invention provides for detection of multiple disturbances along a single fiber. For target disturbances that are not simultaneous (i.e., temporally spaced by the characteristic decay time for a typical system disturbance), then it should be possible to use the arrangement as shown in FIG. 2 with some processing modifications. Such processing changes would be known to one of ordinary skill in the art without undue experimentation. However, any such processing modifications would be nominal if target disturbances are widely separated in time. Whereas, if target disturbances are closely separated in time, processing modifications might require having to shorten averaging time so not to average the multiple target disturbances together. Alternative processing means as described hereinbelow could also be used, for example interrogating both ends of a fiber encircling a perimeter in order to identify two disturbance locations, using an optical switch. If the events were simultaneous, it would be expected that the complexity of the polarisation analysis would have to increase to using a polarimeter type instrument (such as disclosed in PCT Publication WO02095349 filed by Rogers on Nov. 29, 2002) in the receiver leg to calculate the true state-of-polarisation (SOP) and degree-of-polarisation (DOP) of the light as it propagates down the fiber.

In most situations, the arrangement of FIG. 2 would be sufficient and most cost-effective. Additionally, a number of variations on the system shown in FIG. 2 exist that will improve the signal-to-noise (and hence speed) of the system or increase the range and resolution of the system. Additional elements used could be adapted from known radar-based signal processing applications such as those found in U.S. Pat. No. 4,091,367 issued to Harman on May 23, 1978 and U.S. Pat. No. 4,952,939 issued to Seed on Aug. 28, 1990. For example, the received time response data can be grouped into discrete cells corresponding to length segments along the cable. Individual alarm thresholds could be set corresponding to each cell, related to the intruder sensitivity required at these cell locations, for example to give a chosen probability of detection for intruders. In illustration, one could set a high threshold where detection may not be required at a gate, or a low threshold for a cell along a fence section that has low intruder response.

Figure 4:
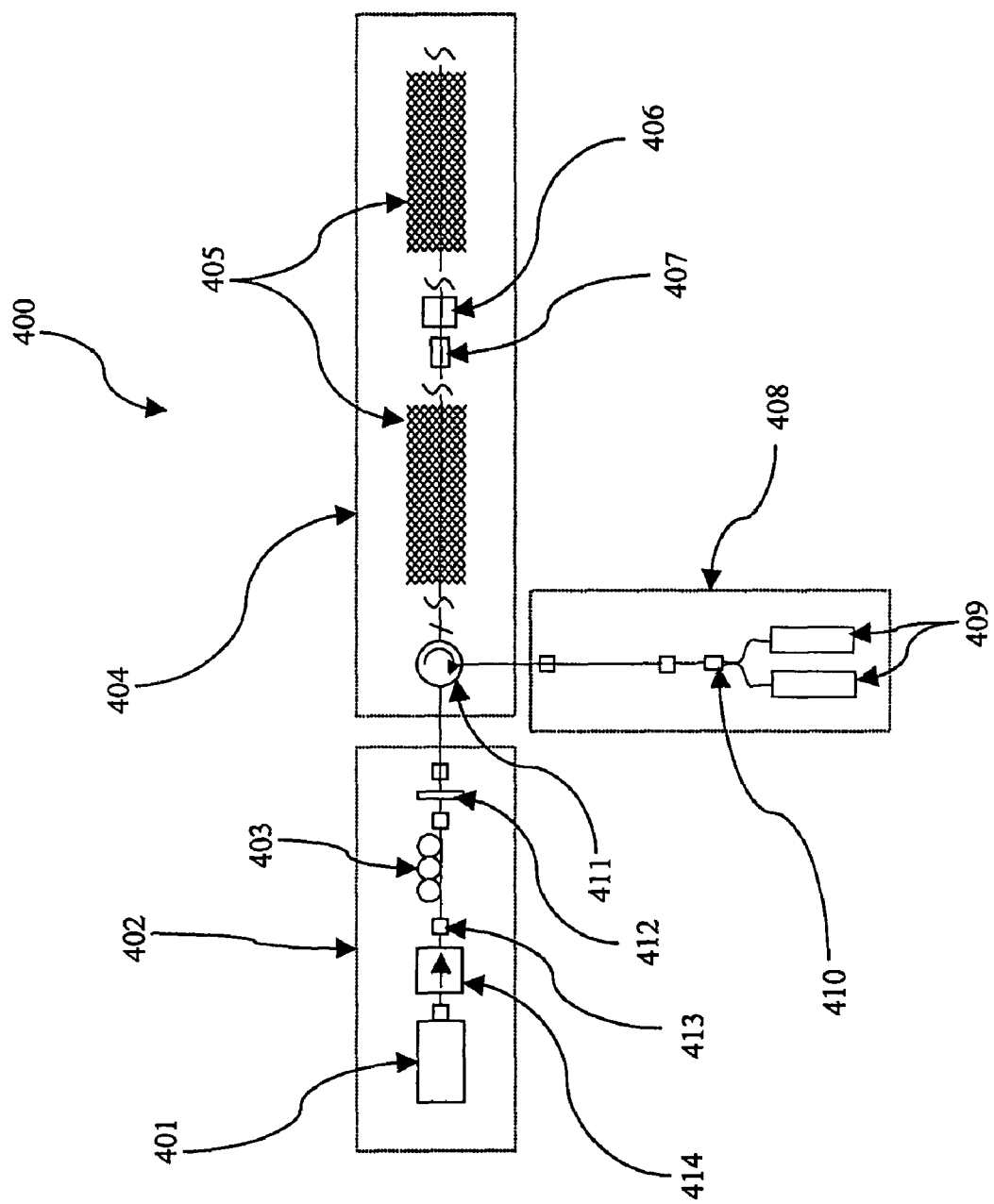
FIG. 4 is a POTDR fiber optic ranging system for intruder detection in accordance with a second preferred embodiment of the present invention.

FIG. 4 shows a second embodiment of the present invention in terms of a relatively more complex system 400 that would realize a longer range. This system 400 includes an optical isolator 414 after the transmitter 401 in the transmitter leg 402 that suppresses any unwanted back reflections from re-entering the transmitter 401 and destabilizing it. An optical tap could also be used (not shown) to monitor the transmitter power stability. A polarisation controller 403 and polarizer 412 could be used to ensure that the light launched into the sensor fiber has maximum power with a good DOP. A further polarisation controller (not shown) could be inserted just before the optical circulator 411 in order to vary the SOP of the light launched into the sensor fiber. The circulator 411 has replaced the directional coupler 212 of FIG. 2; this will realize an approximate 6 dB gain on the received signal.

An optical amplifier 407 and PMD compensator 406 have been inserted into the sensor fiber in the sensor leg 404 between sections of chain link fence 405 in order to compensate for fiber attenuation and depolarization, respectively. Again, while fencing 405 is shown as the carrier mechanism, it should be understood that any suitable element may be used to support the fiber. As well, any number of optical amplifiers 407 and PMD compensators 406 can be used along the sensor fiber length. These would be placed at locations where the attenuation and depolarization fall to unacceptable levels and have to be boosted in order to ensure the sensor keeps working. In the receiver leg 408, the polarisation splitter 410 allows one to choose the maximum of the two orthogonal polarization states for maximum SNR or otherwise choose different processing—i.e., process the difference signal. Other, more complex polarimeter type analysis could be used with the correct choice of components in the receiver leg 408.

Although the present invention is only described in terms of a fiber optic polarisation sensor that operates in the time domain, someone versed in the art would realize that equivalent reflectometry processing in the frequency domain—polarization optical frequency domain reflectometry (POFDR) (both coherent and incoherent) could be utilized without straying from the intended scope of the present invention.

Field tests have been conducted for a demonstrator sensor system constructed based on the technique outlined herein where detection of a single disturbance at ranges up to 2 km with an accuracy of ±2 m and update rates of less than 0.5 second occurred. Longer distances, better accuracy, and faster update rates could easily be achieved without undue experimentation by the correct component selection and signal processing.

For an outdoor perimeter intrusion fence detection sensor, the sensor fiber should be appropriately jacketed in an outdoor rated jacket, which can accommodate temperature extremes and solar ultraviolet (UV) radiation. This jacketed sensor cable would typically be linearly deployed on a fence fabric using UV resistant cable ties and used to detect an intruder, typically when the intruder attempts to cut or climb the fence. Multiple passes and different cable deployment architecture can be used to increase sensitivity or aid fiber repair (i.e., service loops). For example, the cable could be formed into multi-revolution loops on each panel to increase polarisation change from a fence fabric displacement. Because the sensitivity of the fence with attached cable typically varies along the length of the perimeter, it would be advantageous to control the alarm threshold as a function of length in order to reduce the occurrence of false alarms.

With the sensing according to the present invention, it will be possible to vary this threshold as a function of length; this is a capability that prior art non-ranging sensors do not currently have. For example, if a section of fence exists on which there is either insufficient signal or excessive noise, then a lower or higher threshold can be applied, respectively. Insufficient signalling may occur on a section of fence if the mechanical coupling between the cable and fence fabric is low. Excessive noise may occur if vegetation is too close to the fence fabric or the fabric is excessively loose. As well, the present inventive system could be used to detect the location of the excess noise, which might cause false alarms, as an aid to remedy the sensor system installation.

The perimeter security application described herein for the POTDR sensor is typically for a fence-mounted detection system as shown in FIG. 2 and FIG. 4. However, other deployments including buried and surface (e.g., wall-top) mounted fiber optic sensor cables could be also used for detection systems. They also could be used within the walls of buildings to detect intrusion attempts. Such systems have been developed in the past for non-ranging fiber optic detection systems or copper-cable based detection systems and are equally applicable to the present invention.

Figure 5:
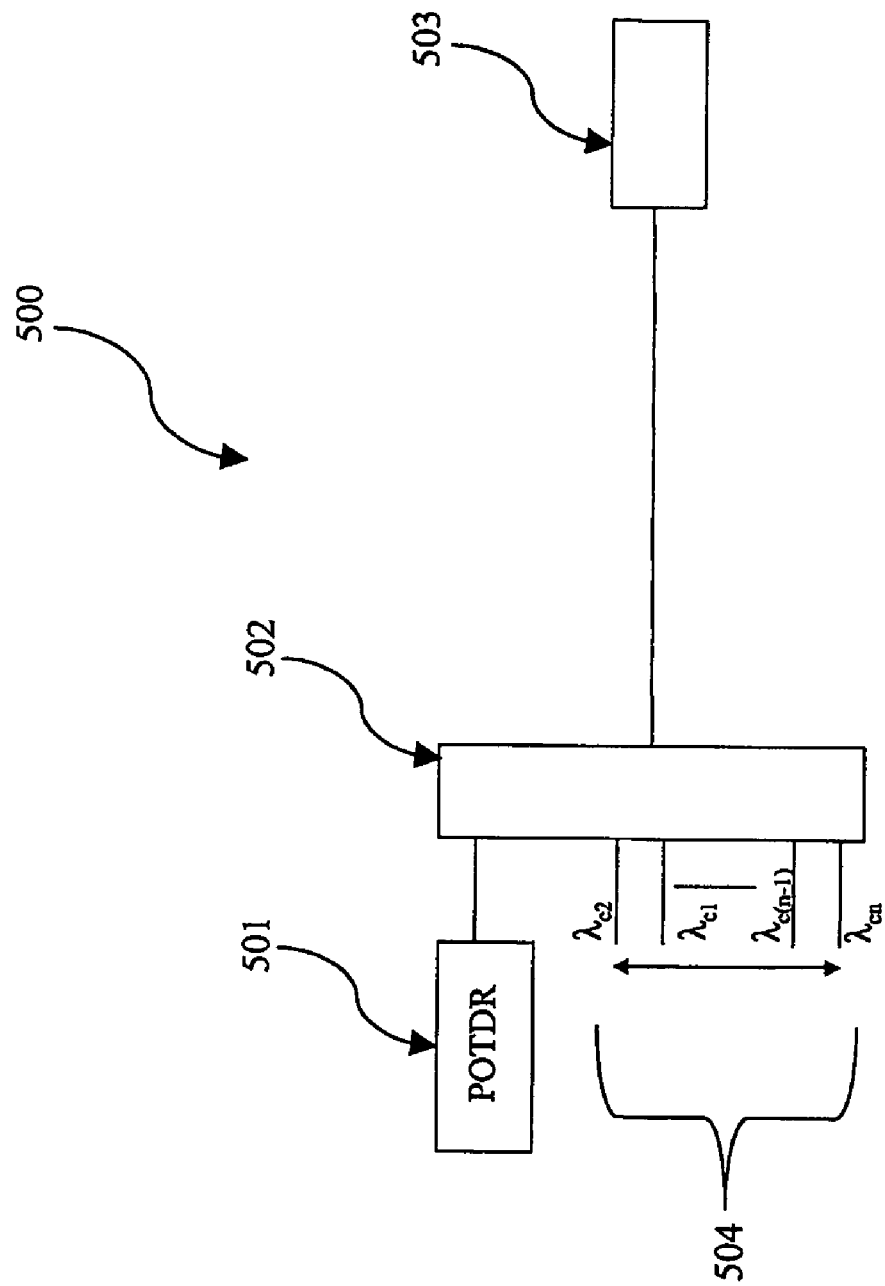
FIG. 5 is a schematic illustrating the present invention integrated into a fiber optic communications system.

Another application of the present invention is for secure telecommunication systems. This architecture 500 is illustrated in FIG. 5. Introducing a small, low-loss bend into the fiber can be used to easily breach the security of a fiber optic telecommunications link. When the fiber is bent, some of the light from the core is lost and this lost light can be captured on a receiver 503 and the information in the fiber accessed. The losses introduced by this bend need not be large and can be so small that conventional OTDR cannot detect the loss. However, the added sensitivity of the POTDR device 501 will enable the present invention to detect these security-breaching bends. Also, a section of the cable would have to be stripped in order to tap into the communications fiber. This would cause a disturbance to the fiber that would not be detected using OTDR, but would easily be detected using POTDR. Wavelength division multiplexing techniques can be used to introduce the POTDR sensor wavelength without compromising the integrity of the telecommunications channels 504. For an electrically based communications system (i.e., using a copper cable based twisted pair), an optic fiber could be incorporated into the cable for security applications.

A further application of the POTDR based system of the present invention described herein would be for pipeline security. A POTDR sensor fiber could be buried on or adjacent to a pipeline carrying for example gas, water, or oil. If a third party intrusion occurs (e.g., digging), or a failure of the pipe occurs, then the ground disturbance created would disturb the fiber inducing a polarisation change within the fiber which could be located by the POTDR sensor. Appropriate response or corrective action could then be quickly taken.

Still a further application for this sensor could be as a fire sensor. A dynamic temperature change to the sensor fiber will also induce a polarisation change within the sensor fiber. The POTDR sensor described in this application will be able to detect and locate this fire induced temperature change.

One disadvantage of a reflectometric fiber optic sensor is that the magnitude of the signal reflected due to Rayleigh backscattering is very small. Because of the weak backscatter signal, some sort of averaging or coding techniques are normally required. These averaging techniques and other limitations such as practical laser sources, and the length of the fiber interrogated, define the maximum speed of the system. For some security applications, an audio output may be desired that is indicative of the disturbance to the sensor cable. An operator may use this additional information to further assess or classify the disturbance cause. In this case, the bandwidth of the POTDR based sensor may be insufficient. One method of providing an audio output along with the disturbance location is to combine any other non-locating optical fiber sensor that has sufficient bandwidth to generate an audio signal and the novel POTDR location sensor described in this application into one hybrid cable sensor.

In one exemplary operation, the present invention embodies a method of detecting a disturbance at a determinable portion along a length of optical fiber using backscattered optical signals that provide polarization change and timing information sufficient to determine a location of the disturbance. As mentioned, the polarization change and timing information includes changes between sampled traces (or time waveforms) that represent normal conditions without the occurrence of a disturbance and the disturbance traces that represent intermittent conditions with the occurrence of a disturbance. The present inventive method involves capturing a predetermined number of reflected polarized signal traces from an optical fiber, digitally filtering the predetermined number of reflected polarized signal traces to form a plurality of digitally filtered traces, and averaging the digitally filtered traces to form an average trace. Such average trace is considered to represent normal conditions. There-after, a disturbance trace is obtained from the optical fiber and compared to the average trace so as to determine a disturbance at a portion of the optical fiber. It should be understood that the disturbance trace itself could be formed by one or more disturbance traces that are digitally filtered and averaged.

Figure 6:
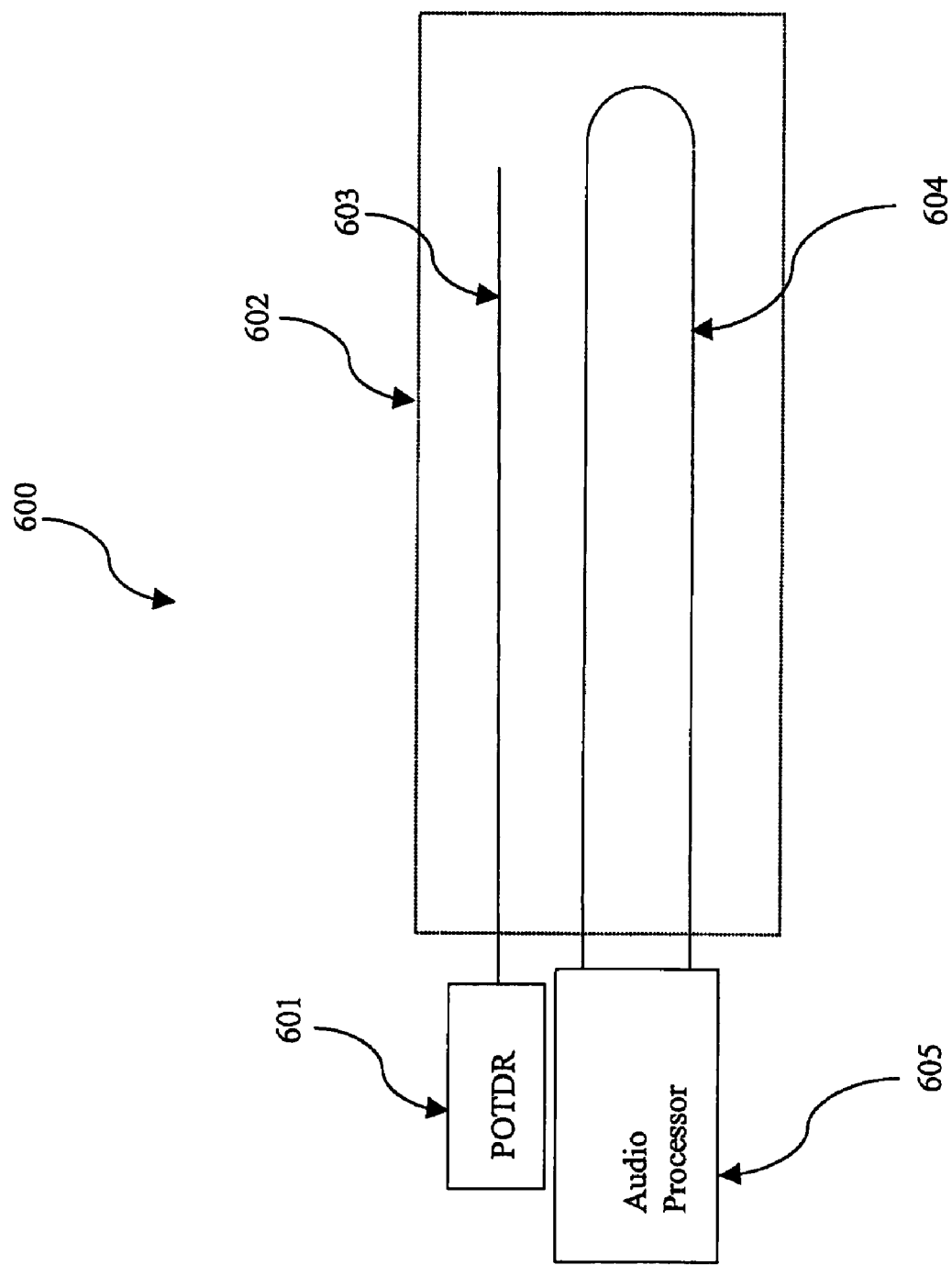
FIG. 6 is a schematic illustrating the present invention integrated into a location intrusion sensor to also provide audio.
Figure 7:
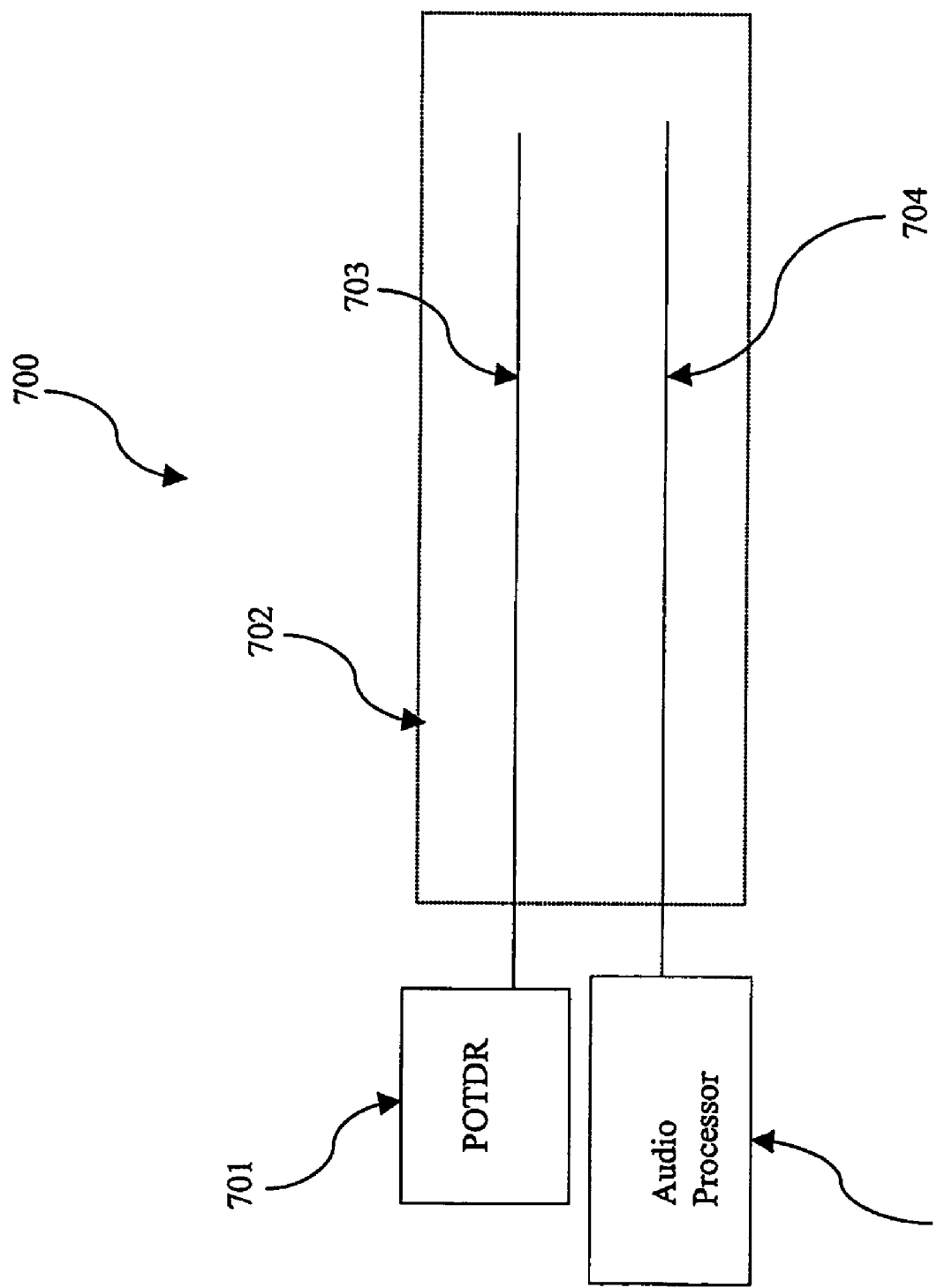
FIG. 7 is a schematic illustrating the present invention integrated into an electrical disturbance sensor to also provide audio.

FIGS. 6 and 7 show schematics of hybrid audio/location sensor 600 and 700, respectively. The sensor could include any non-locating optical fiber sensor cable 604 (as in FIG. 6) or non-locating electrically based sensor cable 704 (as in FIG. 7) that renders additional intruder response information such as an audio output indicative of a disturbance. FIG. 6 illustrates a method of providing an audio output with location by combining the current IntelliFIBER™ sensor (as shown in FIG. 1) and the novel POTDR location sensor 601 and related location fiber 603 described in this application into one hybrid cable. While one hybrid cable is preferred, it should be noted that two separate cables could be deployed beside each other without straying from the intended scope of the present invention. Although a loop 604 is shown, it should be understood that such fiber could be open-ended with transmit at one end, receive at opposing remote end. Elements 604 and 704 may or may not be a loop; sometimes a loop may be used in certain instances such as, but not limited to, tall fences with two cable passes, or to have the entire processing all in one spot. Such variations are well within the intended scope of the present invention. The IntelliFIBER™ optical sensor loop 604 and processor 605 in FIG. 6 could also be replaced with any other non-locating optical fiber sensor and processor (such as those produced by Fiber SenSys, Inc, of Beaverton, Oreg., US or by Future Fibre Technologies Pty. Ltd., Rowville, Victoria, Australia).

The IntelliFIBER™ optical sensor loop 604 and processor 605 in FIG. 6 could also be replaced with any other non-locating electrically-based sensor cable and processor along with the novel POTDR location sensor 701 to give the audio output as in FIG. 7. Such electrically based non-locating sensors are copper based electrical intrusion sensors that would rely on different sensing principles using cables 704 in a variety of forms depending on the sensing principle. For example, the cables could include coaxial cables with loose conductors, multi-conductor copper cables, twin-lead conductors, or the like each utilizing some known signal generating or modification means such as triboelectric, piezoelectric, magnetic, or electret principles. Such cables can be in a loop or be provided with sensing electronics at opposing ends—dependent on their sensing principles and application. If a single loop is provided, then the fiber sensor electronics can be limited to at a single location joining the loop ends. Such electrically based sensors also include triboelectric intrusion sensors as produced by Senstar-Stellar of Carp, Ontario, Canada and marketed under the name IntelliFLEX™ that provide an audio output and exploits the tribo-electric effect in a coaxial cable.

It should be readily understood that there could be other data signals obtained from the two independent sensors (i.e., the inventive POTDR location sensor and the intrusion sensor (electrical or optical) where such other data signals could be fused together to provide better intruder detection. For example, the audio is essentially the time response magnitude to an intrusion event at up to audio frequencies, as the sensor cables act as distributed linear microphones. This magnitude data time correlated to the fiber response data from the inventive POTDR location sensor is a further indication of a valid intrusion. In other words, the data from the inventive POTDR location sensor and the intrusion sensor (whether electrical or optical) are fused to provide enhanced detection and classification of intruders (i.e., disturbances) and their location. In such instances, the elements 601 and 605 in FIG. 6 would be interconnected for processing (not shown), as would the elements 701 and 705 in FIG. 7. Still further, such sensors may also have their data fused in a separate processor (not shown) where the separate processor correlates the intruder signal response from both independent sensor cables 603, 604 or 703, 704 and corresponding detection methods in order to obtain better detection and classification of events. In any instance, it should be readily understood that the POTDR and audio processors could be either separate or integrated without straying from the intended scope of the present invention.

Of course, with further developments in the optical components and processing, a direct audio output from the POTDR sensor may be economically possible in the future, and with sufficient bandwidth could give the audio as a function of location. In all cases, the different fiber or copper cables could be combined within the same overjacket 602, 702.

Figure 8:
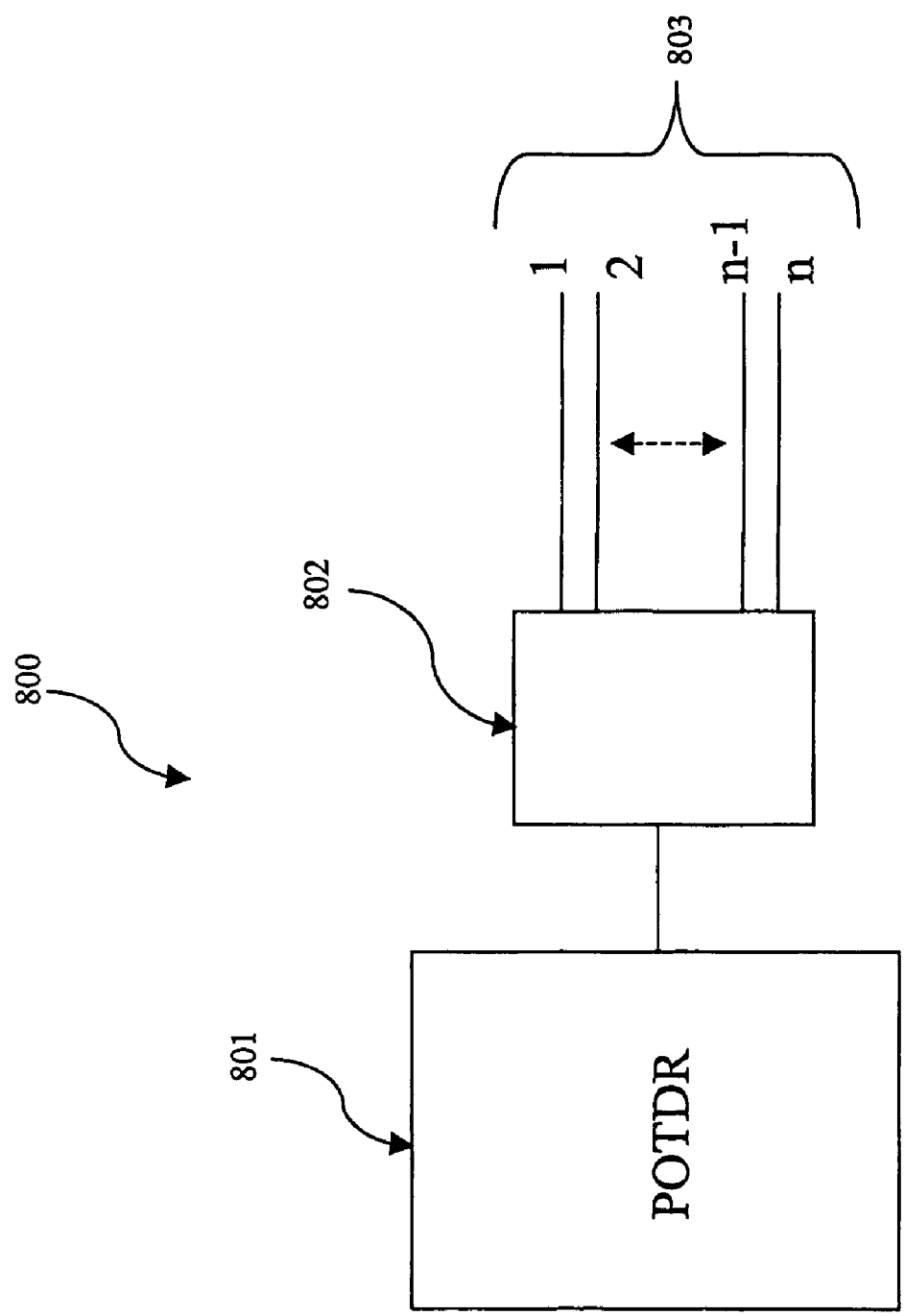
FIG. 8 is a POTDR fiber optic ranging system for intruder detection in accordance with a third preferred embodiment of the present invention and including an optical switch.

A further architecture 800 of the above sensor is to use an optical switch 802 and multiple sensor fibers 803 as shown in FIG. 8. In this multiplexed option, the power from the POTDR laser source 801 is shared between multiple sensor fibers 803 using a switch 802 that would sequentially address sensor fibers 803 that are located on different parts of a perimeter. This shared use reduces the cost of electronics per fiber. The present invention could also be employed to interrogate a single fiber from opposite ends or multiple fibers in parallel, which may be in a shared or separate jacket. This is useful, for example, to detect multiple intrusion events along a perimeter, where a loop with a single or multiple fibers encircles the entire perimeter.

Finally, in some situations it may be advantageous to remotely locate the optoelectronic components and have insensitive fiber optic downleads to the sensor cable. This can be accomplished in a number of ways including:

a. constructing the downleads from highly birefringent fiber and propagating the light in either the fast or slow axis only;
b. using standard single mode fiber housed in a protective conduit;
c. using standard single mode fiber housed in a protective conduit and ignoring the signal from the downlead section of the ranging sensor;
d. simply ignoring the signal from the downlead section of the ranging sensor if signals were not simultaneous with a downstream event (because one would know to ignore the event in the downlead due to prior knowledge that there is nothing there because it is the downlead); and
e. moving the polarisation analyzing components out in the field (i.e., fiber polarizer in FIG. 2 or polarisation splitter in FIG. 4) and using regular single mode fiber to remotely connect to the other optical components (i.e., laser source and photodiodes).

It should be understood that the preferred embodiments mentioned here are merely illustrative of the present invention. Numerous variations in design and use of the present invention may be contemplated in view of the following claims without straying from the intended scope and field of the invention herein disclosed.

The invention claimed is:

1. An intrusion detection system for detecting a disturbance at a determinable portion of a structure comprising:
   (a) transmitter leg for launching a wavelength invariant pulsed polarized optical signal;

(b) a sensor leg for arrangement along the structure, the sensor leg comprising a sensing optical fiber to carry a portion of said polarized optical signal sensitive to a disturbance therealong; and (c) a receiver leg for receiving a portion of a backscattered optical signal from said sensor leg;

wherein said backscattered optical signal provides polarization change and timing information relative to said pulsed polarized optical signal, sufficient to determine a location of the disturbance along said sensor leg; and wherein the location of the disturbance along the sensor leg can be mapped to the determinable portion of the structure.

2. The system as claimed in claim 1, wherein said transmitter leg includes a polarized pulsed optical source;

said receiver leg includes a polarizer and a receiver for processing a signal received from said sensing optical fiber; and said transmitter leg, receiver leg, and said sensor leg are coupled together via a directional coupler.

3. The system as claimed in claim 1, wherein said transmitter leg includes a transmitter, an isolator, a polarization controller, and a polarizer;

said sensor leg includes at least one optical amplifier, and a polarization mode dispersion compensator;

said receiver leg includes a polarization splitter and a plurality of receivers for processing a signal received from said sensing optical fiber; and said transmitter leg, receiver leg, and said sensor leg are coupled together via a circulator.

4. The as claimed in claim 3, wherein the sensor leg comprises at least two optical amplifiers and at least two polarization mode dispersion compensators.

5. The system as claimed in claim 1, wherein said intrusion detection is operatively coupled to an optical telecommunications cable for detecting tampering with said optical telecommunications cable.

6. The system as claimed in claim 1, wherein said intrusion detection system is operatively coupled to a non-ranging perimeter security sensing cable for detecting disturbances along its length.

7. The system as claimed in claim 6, wherein said non-ranging perimeter security sensing cable is optically based.

8. The system as claimed in claim 6, wherein said non-ranging perimeter security sensing cable is electrically based.

9. The system as claimed in claim 1, wherein said intrusion detection system further comprises an optical switch operatively coupled to the transmitter leg, the sensor leg, and the receiver leg for sensing disturbances along a plurality of sensor legs.

10. The system as claimed in claim 1, wherein said sensor leg is hybrid cable comprising:

said sensing optical fiber; and a non-locating sensor cable for generating an electrical signal capable of being processed into an audio output indicative of a disturbance along said non-locating sensor cable;

wherein said sensing optical fiber and non-locating sensor cable are physically integrated within a single jacket.

11. The system as claimed in claim 1, wherein said sensor leg is a hybrid cable comprising:

said sensing optical fiber; and a non-locating sensor cable for modifying a signal cable of being processed into an audio output indicative of a disturbance along said non-locating sensor cable;

wherein said sensing optical fiber and non-locating sensor cable are physically integrated within a single jacket.

12. The system as claimed in claim 11, wherein said non-locating sensor cable is an optical cable for modification of the signal.

13. The system as claimed in claim 11, wherein said non-locating sensor cable is electrically based for modification of the signal.

14. The system as claimed in claim 1, wherein said structure is selected from at least one member of the group consisting of a fence, a pipeline, a building, a wall, and a wall-top.

15. A method of detecting a disturbance at a determinable portion along a length of optical fiber using backscattered optical signals that provide polarization change and time information sufficient to determine a location of said disturbance, said method comprising:

launching a pulsed polarized optical signal for carrying within an optical fiber;

capturing a predetermined number of reflected polarized signal traces from said optical fiber;

digitally filtering said predetermined number of reflected polarized signal traces to form a plurality of digitally filtered traces;

averaging said digitally filtered traces to form an average trace;

obtaining a disturbance trace from said optical fiber; and comparing said disturbance trace to said average trace so as to determine a disturbance at a portion of said optical fiber.

16. The method as claimed in claim 15, wherein said obtaining step includes filtering and averaging one or more disturbance traces.

17. An intrusion detection system for detecting an intrusion along a determinable portion of a structure comprising:

(a) a transmitter leg for launching a wavelength invariant pulsed polarized optical signal;

(b) a sensor leg for arrangement along the structure, the sensor lea comprising a sensor cable including a locating optical fiber to carry a portion of said pulsed polarized optical signal sensitive to a disturbance therealong and a non-locating sensor cable;

(c) a receiver leg for accepting a portion of a backscattered optical signal from said sensor leg; and (d) a signal processor for providing a signal response output indicative of a disturbance along said non-locating sensor cable;

wherein said backscattered optical signal provides polarization change and timing information relative to said pulsed polarized optical signal sufficient to determine a location of the disturbance along the locating optical fiber; and wherein the location of the disturbance along the sensor leg can be mapped to the determinable portion of the structure.

18. The system as claimed in claim 17 wherein signal response output and said polarization change and timing information are processed together to provide enhanced detection, location, and classification of the disturbances.

19. The system as claimed in claim 17, wherein said optical fiber and said non-locating sensor cable are physically integrated within a single jacketing.

20. The system as claimed in claim 17, wherein said non-locating sensor cable generates an electrical signal which is capable of being processed into an audio output indicative of a disturbance along said non-locating sensor cable.

21. The system as claimed in claim 17, wherein said non-locating sensor cable modifies a signal which is capable of being processed into an audio output indicative of a disturbance along said non-locating sensor cable.

22. The system as claimed in claim 21, wherein said non-locating sensor cable is an optical fiber for modification of the signal.

23. The system as claimed in claim 21 wherein said non-locating sensor cable is electrically based for modification of the signal.

\* \* \* \* \*